US009763909B2

(12) United States Patent
St. Laurent et al.

(10) Patent No.: US 9,763,909 B2
(45) Date of Patent: Sep. 19, 2017

(54) METHODS FOR TREATING INFLAMMATION AND PAIN

(71) Applicant: Olatec Therapeutics LLC, New York, NY (US)

(72) Inventors: Joseph P. St. Laurent, Lakeville, MA (US); Gerald S. Jones, Norwood, MA (US); David M. Bresse, Middleboro, MA (US); George M. Shopp, Jr., Boulder, CO (US)

(73) Assignee: Olatec Therapeutics LLC, New York, NY (US)

( * ) Notice: Subject to any disclaimer, the term of this patent is extended or adjusted under 35 U.S.C. 154(b) by 0 days.

(21) Appl. No.: 15/363,384

(22) Filed: Nov. 29, 2016

(65) Prior Publication Data

US 2017/0143660 A1 May 25, 2017

Related U.S. Application Data

(60) Division of application No. 14/644,063, filed on Mar. 10, 2015, which is a continuation-in-part of application No. PCT/US2013/059094, filed on Sep. 10, 2013.

(60) Provisional application No. 61/699,720, filed on Sep. 11, 2012, provisional application No. 61/955,683, filed on Mar. 19, 2014.

(51) Int. Cl.

| | |
|---|---|
| ***A61K 31/275*** | (2006.01) |
| ***A61K 31/485*** | (2006.01) |
| ***A61K 9/00*** | (2006.01) |

(52) U.S. Cl.
CPC .......... *A61K 31/275* (2013.01); *A61K 9/0053* (2013.01); *A61K 31/485* (2013.01)

(58) Field of Classification Search
CPC ... A61K 31/275; A61K 31/485; A61K 9/0053
See application file for complete search history.

(56) References Cited

U.S. PATENT DOCUMENTS

| | | | | |
|---|---|---|---|---|
| 4,219,569 A | | 8/1980 | Glenn | |
| 4,424,167 A | | 1/1984 | Oeckl | |
| 4,863,960 A | | 9/1989 | Donofrio et al. | |
| 2005/0124590 A1 | * | 6/2005 | Kuwada | A61K 31/095 514/114 |
| 2005/0159439 A1 | * | 7/2005 | Pappagallo | A61K 9/0014 514/282 |
| 2006/0148732 A1 | | 7/2006 | Gutterman et al. | |

FOREIGN PATENT DOCUMENTS

| | | | | |
|---|---|---|---|---|
| WO | WO 2004112819 A1 | * | 12/2004 | A61K 36/00 |
| WO | 2011-130395 A1 | | 10/2011 | |

OTHER PUBLICATIONS

Search Report dated Dec. 23, 2013 in PCT/US2013/059094.

Ghanim, H. et al., "Suppression of Nuclear Factor-kB and Stimulation of Inhibitor kB by Troglitazone: Evidence for an Antiinflammatory Effect and a Potential Antiatherosclerotic Effect in the Obese", The Journal of Clinical Endocrinology & Metabolism, 2001, vol. 86, pp. 1306-1312.

Kubota, S. et al., "Prevention of Ocular Inflammation in Endotoxin-Induced Uveitis with Resveratrol by Inhibiting Oxidative Damage and Nuclear Factor—KB Activation", Investigative Ophthalmology & Visual Science, 2009, vol. 50, No. 7, pp. 3512-3519.

Bonnett, et al., Rheumatology, 2004, British Society for Rheumatology, vol. 44(1), pp. 7-16.

* cited by examiner

*Primary Examiner* — Sarah Pihonak
(74) *Attorney, Agent, or Firm* — Perkins Coie LLP; Viola T. Kung

(57) ABSTRACT

The present invention is directed to a pharmaceutical composition comprising a pharmaceutically acceptable carrier and an ω-(methanesulfonyl)alkenylnitrile compound, or a pharmaceutically acceptable salt thereof. The present invention is also directed to a method for treating inflammation, inflammatory-related disorders, or pain, by administering an ω-(methanesulfonyl)alkenylnitrile compound or a pharmaceutically acceptable salt or solvate thereof to a subject in need thereof. The present invention is further directed to a method for potentiating the analgesic effects of morphine, by administering an effective amount of 3-(methylsulfonyl) acrylonitrile to a subject who is being treated with morphine and is suffering from pain. Oral and topical administration are preferred.

5 Claims, 1 Drawing Sheet

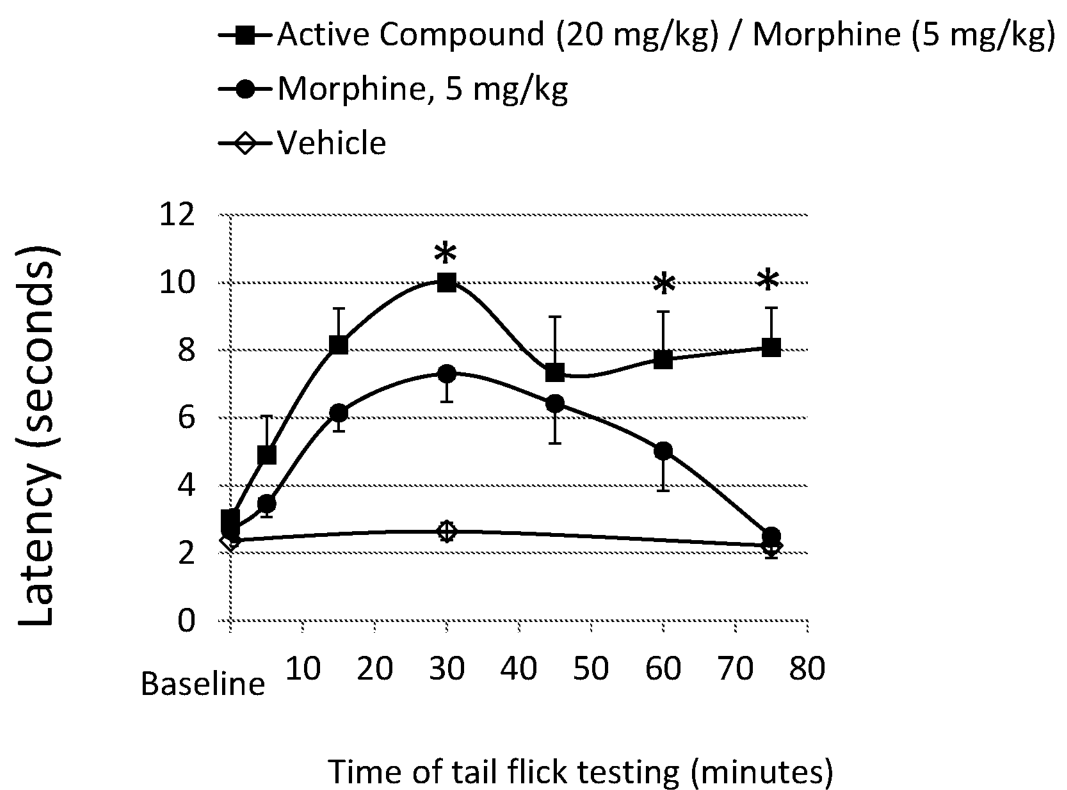
Active Compound (20 mg/kg) / Morphine (5 mg/kg)
Morphine, 5 mg/kg
Vehicle
Latency (seconds)
12
10
8
6
4
2
0
*
*
*
Baseline
10
20
30
40
50
60
70
80
Time of tail flick testing (minutes)

METHODS FOR TREATING INFLAMMATION AND PAIN

This application is a divisional of U.S. application Ser. No. 14/644,063, filed Mar. 10, 2015; which claims the priority of continuation-in-part of PCT/US2013/059094, filed Sep. 10, 2013; which claims the priority of U.S. Provisional application No. 61/699,720, filed Sep. 11, 2012. U.S. application Ser. No. 14/644,063 also claims the benefit of U.S. Provisional application No. 61/955,683, filed Mar. 19, 2014. The above-identified applications are incorporated herein by reference in their entireties.

FIELD OF THE INVENTION

The present invention relates to a pharmaceutical composition comprising a pharmaceutically acceptable carrier and an ω-(methanesulfonyl)alkenylnitrile compound, or its pharmaceutically acceptable salts. The present invention also relates to methods of using the compound for treating inflammation or inflammatory-related disorders and pain. The present invention also relates to a method for potentiating the analgesic effects of morphine. Oral and topical routes of administration are preferred.

BACKGROUND OF THE INVENTION

Inflammation is a process by which microbes or tissue injury induce the release of cytokines and chemokines from various cell types producing increased blood vessel permeability, upregulation of endothelial receptors, and thus increased egress of various cells of the innate and adaptive immune system which enter surrounding tissue and grossly produce the classical picture of inflammation, i.e. redness, swelling, heat and pain.

Inflammation is a localized reaction of live tissue due to an injury, which may be caused by various endogenous and exogenous factors. The exogenous factors include physical, chemical, and biological factors. The endogenous factors include inflammatory mediators, antigens, and antibodies. Endogenous factors often develop under the influence of an exogenous damage. An inflammatory reaction is often followed by an altered structure and penetrability of the cellular membrane. Endogenous factors, such as mediators and antigens define the nature and type of an inflammatory reaction, especially its course in the zone of injury. In the case where tissue damage is limited to the creation of mediators, an acute form of inflammation develops. If immunologic reactions are also involved in the process, through the interaction of antigens, antibodies, and autoantigens, a long-term inflammatory process will develop. Various exogenous agents, for example, infection, injury, radiation, also provide the course of inflammatory process on a molecular level by damaging cellular membranes which initiate biochemical reactions.

Based on the physical causes, pain can be divided into three types: nociceptive, neuropathic, and mix-type.

Nociceptive pain is the term for pain that is detected by specialized sensory nerves called nociceptors. These nerves are located throughout the soft tissues, such as muscles and skin, as well as the internal organs. There are two types of nociceptive pain: somatic pain and visceral pain. Visceral pain comes from the internal organs. Deep somatic pain is initiated by stimulation of nociceptors in ligaments, tendons, bones, blood vessels, fasciae and muscles, and is dull, aching, poorly localized pain. Examples include sprains and broken bones. Superficial pain is initiated by activation of nociceptors in the skin or other superficial tissue, and is sharp, well-defined and clearly located. Examples of injuries that produce superficial somatic pain include minor wounds and minor (first degree) burns. Nociceptive pain is usually short in duration and end when the damage recovers. Examples of nociceptive pain include postoperative pain, sprains, bone fractures, burns, bumps, bruises, and inflammatory pain.

Neuropathic pain is pain caused by damage or disease that affects the somatosensory system. Neuropathic pain is originated from spontaneous ectopic neuron discharge in the nervous system either in central or in peripheral. Because the underlying etiologies are usually irreversible, most neuropathic pain are chronic pain. Most people describe neuropathic pain as shooting, burning, tingling, lancinating, electric shock qualities, numbness, and persistent allodynia. The nomenclature of neuropathic pain is based on the site of initiating nervous system with the etiology; for examples, central post-stroke pain, diabetes peripheral neuropathy, post-herpetic (or post-shingles) neuralgia, terminal cancer pain, phantom limb pain.

Mix-type pain is featured by the coexistence of both nociceptive and neuropathic pain. For example, muscle pain trigger central or peripheral neuron sensitization leading to chronic low back pain, migraine, and myofacial pain.

Connective tissues are subjected to a constant barrage of stress and injury. Acute or chronic impacts and the natural progression of various degenerative diseases all produce painful inflammation in joint regions, such as the neck, back, arms, hips, ankles and feet. These afflictions are common and often debilitating.

Current therapy is directed to some or all of the pathogenetic components of inflammation. For example, corticosteroids have a broad spectrum of activities and NSAIDS are more specifically anti-prostaglandin and analgesic. All current therapies have relatively high rates of adverse effects and adverse effects are severe and serious.

There is a need for a composition and a method for treating inflammation, inflammatory-related disorders, and pain. The composition should be economic and easy to manufacture, and the method should be effective and have no significant side effects.

SUMMARY OF THE INVENTION

The present invention is directed to a pharmaceutical composition comprising a pharmaceutically acceptable carrier and an ω-(methanesulfonyl)alkenylnitrile compound or a pharmaceutically acceptable salt or solvate thereof. The compound is at least 90% pure (w/w).

The present invention is also directed to a method for treating inflammation, inflammatory-related disorders, and pain. The method comprises the step of administering an ω-(methanesulfonyl)alkenylnitrile compound or a pharmaceutically acceptable salt thereof to a subject in need thereof. The pharmaceutical composition comprising the active compound can be applied by any accepted mode of administration including oral, topical, and parenteral (such as intravenous, intramuscular, subcutaneous or rectal). Oral and topical administration are preferred.

BRIEF DESCRIPTION OF THE FIGURES

FIG. 1 shows the latency in seconds of mouse tail flick when measured at 0, 5, 15, 30, 45, 60, and 75 minutes post morphine dosing. The mice were treated with vehicle, morphine alone, or morphine plus the active compound 3-(methylsulfonyl)acrylonitrile. The active compound was dosed an hour before morphine dosing.

DETAILED DESCRIPTION OF THE INVENTION

Definition

"Alkyl" refers to groups of from 1 to 12 carbon atoms, either straight chained or branched, preferably from 1 to 8 carbon atoms, and more preferably 1 to 6 carbon atoms.

"Arylalkyl" refers to aryl-alkyl-groups preferably having from 1 to 6 carbon atoms in the alkyl moiety and from 6 to 10 carbon atoms in the aryl moiety. Such arylalkyl groups are exemplified by benzyl, phenethyl and the like.

"Cycloalkyl" refers to cyclic alkyl groups of from 3 to 12 carbon atoms having a single cyclic ring or multiple condensed rings which can be optionally substituted with from 1 to 3 alkyl groups. Such cycloalkyl groups include, by way of example, single ring structures such as cyclopropyl, cyclobutyl, cyclopentyl, cyclooctyl, 1-methylcyclopropyl, 2-methylcyclopentyl, 2-methylcyclooctyl, and the like, or multiple ring structures such as adamantyl, and the like.

"Pharmaceutically acceptable salts," as used herein, are salts that retain the desired biological activity of the parent compound and do not impart undesired toxicological effects.

Pharmaceutically acceptable salt forms include various crystalline polymorphs as well as the amorphous form of the different salts. The pharmaceutically acceptable salts can be formed with metal or organic counterions and include, but are not limited to, alkali metal salts such as sodium or potassium; alkaline earth metal salts such as magnesium or calcium; and ammonium or tetraalkyl ammonium salts, i.e., $NX_4$+(wherein X is $C_{1-4}$.

"Solvates," as used herein, are addition complexes in which the compound is combined with an acceptable co-solvent in some fixed proportion. Co-solvents include, but are not limited to, ethyl acetate, lauryl lactate, myristyl lactate, cetyl lactate, isopropyl myristate, ethanol, 1-propanol, isopropanol, 1-butanol, isobutanol, tert-butanol, acetone, methyl ethyl ketone, and diethyl ether.

The inventors have discovered that ω-(methanesulfonyl) alkenylnitriles are effective for treating inflammation, inflammatory-related disorders, and pain.

ω-(Methanesulfonyl)alkenylnitriles

ω-(Methanesulfonyl)alkenylnitriles (methanesulfonylalkanenitriles) useful for the present invention are compounds of formula I (both E- and Z-isomers), or a pharmaceutically acceptably salt or solvate thereof:

Formula I

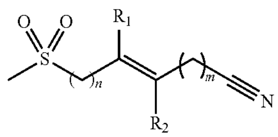

wherein $R_1$ and $R_2$ are independently selected from the group consisting of H, straight-chain alkyl, branched alkyl, cycloalkyl, and arylalkyl, and halogen; and n=0, 1, 2, 3, 4, 5, 6, 7, 8, or 9; m=0, 1, 2, 3, 4, 5, 6, 7, 8, or 9; and n+m=0-9. Preferably n+m=0-4, more preferably n=0-4 and m=0.

The structures of (E)-methanesulfonylacrylonitrile (1; n=m=0; $R_1$=$R_2$=H; molecular weight MW=131.15), (Z)-methanesulfonylacrylonitrile (2; n=m=0; $R_1$=$R_2$=H; MW=131.15), 2, 3-dichloro-3-methanesulfonylacrylonitrile (3; n=m=0; $R_1$=$R_2$=Cl, MW=200.04), 4-methanesulfonyl-but-2-enenitrile (4; n=1, m=0; $R_1$=$R_2$=H, MW=145.18), 5-methanesulfonylpent-2-enenitrile (5; n=2, m=0; $R_1$=$R_2$=H, MW=159.21), 6-methanesulfonylhex-2-enenitrile (6; n=3, m=0; $R_1$=$R_2$=H, MW=173.23), and 7-methanesulfonylhept-2-enenitrile (7; n=4, m=0; $R_1$=$R_2$=H, MW=187.26) are shown below.

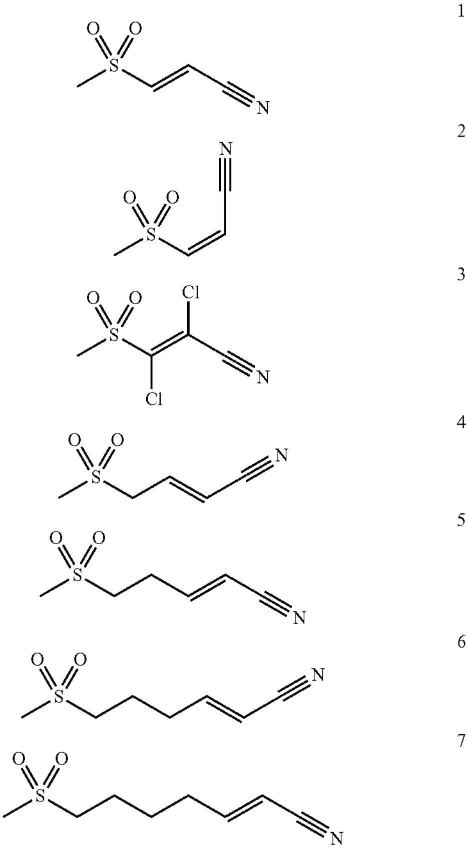

(E)-Methanesulfonylacrylonitrile (1) can be prepared according to U.S. Pat. No. 3,541,119. For example, the compound can be prepared by alkylating sodium methanesulfinate with 2,3-dichloropropionitrile in the presence of a base.

(Z)-Methanesulfonylacrylonitrile (2) can be prepared by modifying the procedure of Asscher and Vofsi (J. Chem. Soc. 1964, 4962-4971). For example, the compound can be prepared by a copper-catalyzed addition of methanesulfonyl chloride to acrylonitrile.

2, 3-dichloro-3-methanesulfonylacrylonitrile (3) can be prepared according to U.S. Pat. No. 4,424,167. For example, the compound can be prepared from 3-methylsulfonylpriopionitrile by a series of chlorination/dehydrohalogenation reactions using chlorine gas in the presence of a basic catalyst.

ω-Methanesulfonylalk-2-enenitriles (e.g. Compounds 4, 5, 6, and 7) can be prepared by alkylating sodium methanesulfinate with requisite ω-halolalk-2-enenitriles, or by alkylating sodium thiomethoxide with the requisite ω-halolalk-2-enenitriles, followed by oxidation of the products with hydrogen peroxide or other appropriate oxidizing agent such as urea hydrogen peroxide.

Pharmaceutical Compositions

The present invention provides pharmaceutical compositions comprising one or more pharmaceutically acceptable carriers and an active compound of ω-(methanesulfonyl) alkenylnitrile, or a pharmaceutically acceptable salt or a solvate thereof. The pharmaceutical composition can include one of the cis or trans isomers, or both isomers either equimolar, or of different amounts. The active compound or its pharmaceutically acceptable salt or solvate in the pharmaceutical compositions in general is in an amount of about 0.01-20%, or 0.05-20%, or 0.1-20%, or 0.2-15%, or 0.5-10%, or 1-5% (w/w) for a topical formulation; about 0.1-5% for an injectable formulation, 0.1-5% for a patch formulation, about 1-90% for a tablet formulation, and 1-100% for a capsule formulation.

In one embodiment, the active compound is incorporated into any acceptable carrier, including creams, gels, lotions or other types of suspensions that can stabilize the active compound and deliver it to the affected area by topical applications. In another embodiment, the pharmaceutical composition can be in a dosage form such as tablets, capsules, granules, fine granules, powders, syrups, suppositories, injectable solutions, patches, or the like. The above pharmaceutical composition can be prepared by conventional methods.

Pharmaceutically acceptable carriers, which are inactive ingredients, can be selected by those skilled in the art using conventional criteria. Pharmaceutically acceptable carriers include, but are not limited to, non-aqueous based solutions, suspensions, emulsions, microemulsions, micellar solutions, gels, and ointments. The pharmaceutically acceptable carriers may also contain ingredients that include, but are not limited to, saline and aqueous electrolyte solutions; ionic and nonionic osmotic agents such as sodium chloride, potassium chloride, glycerol, and dextrose; pH adjusters and buffers such as salts of hydroxide, phosphate, citrate, acetate, borate; and trolamine; antioxidants such as salts, acids and/or bases of bisulfite, sulfite, metabisulfite, thiosulfite, ascorbic acid, acetyl cysteine, cysteine, glutathione, butylated hydroxyanisole, butylated hydroxytoluene, tocopherols, and ascorbyl palmitate; surfactants such as lecithin, phospholipids, including but not limited to phosphatidylcholine, phosphatidylethanolamine and phosphatidyl inositiol; poloxamers and poloxamines, polysorbates such as polysorbate 80, polysorbate 60, and polysorbate 20, polyethers such as polyethylene glycols and polypropylene glycols; polyvinyls such as polyvinyl alcohol and povidone; cellulose derivatives such as methylcellulose, hydroxypropyl cellulose, hydroxyethyl cellulose, carboxymethyl cellulose and hydroxypropyl methylcellulose and their salts; petroleum derivatives such as mineral oil and white petrolatum; fats such as lanolin, peanut oil, palm oil, soybean oil; mono-, di-, and triglycerides; polymers of acrylic acid such as carboxypolymethylene gel, and hydrophobically modified cross-linked acrylate copolymer; polysaccharides such as dextrans and glycosaminoglycans such as sodium hyaluronate. Such pharmaceutically acceptable carriers may be preserved against bacterial contamination using well-known preservatives, these include, but are not limited to, benzalkonium chloride, ethylenediaminetetraacetic acid and its salts, benzethonium chloride, chlorhexidine, chlorobutanol, methylparaben, thimerosal, and phenylethyl alcohol, or may be formulated as a non-preserved formulation for either single or multiple use.

For example, a tablet formulation or a capsule formulation of the active compound may contain other excipients that have no bioactivity and no reaction with the active compound. Excipients of a tablet or a capsule may include fillers, binders, lubricants and glidants, disintegrators, wetting agents, and release rate modifiers. Binders promote the adhesion of particles of the formulation and are important for a tablet formulation. Examples of excipients of a tablet or a capsule include, but not limited to, carboxymethylcellulose, cellulose, ethylcellulose, hydroxypropylmethylcellulose, methylcellulose, karaya gum, starch, tragacanth gum, gelatin, magnesium stearate, titanium dioxide, poly(acrylic acid), and polyvinylpyrrolidone. For example, a tablet formulation may contain inactive ingredients such as colloidal silicon dioxide, crospovidone, hypromellose, magnesium stearate, microcrystalline cellulose, polyethylene glycol, sodium starch glycolate, and/or titanium dioxide. A capsule formulation may contain inactive ingredients such as gelatin, magnesium stearate, and/or titanium dioxide.

For example, a patch formulation of the active compound may comprise some inactive ingredients such as 1,3-butylene glycol, dihydroxyaluminum aminoacetate, disodium edetate, D-sorbitol, gelatin, kaolin, methylparaben, polysorbate 80, povidone, propylene glycol, propylparaben, sodium carboxymethylcellulose, sodium polyacrylate, tartaric acid, titanium dioxide, and purified water. A patch formulation may also contain skin permeability enhancer such as lactate esters (e.g., lauryl lactate) or diethylene glycol monoethyl ether.

Topical formulations including the active compound can be in a form of gel, cream, lotion, liquid, emulsion, ointment, spray, solution, and suspension. The inactive ingredients in the topical formulations for example include, but not limited to, lauryl lactate (emollient/permeation enhancer), diethylene glycol monoethyl ether (emollient/permeation enhancer), DMSO (solubility enhancer), silicone elastomer (rheology/texture modifier), caprylic/capric triglyceride, (emollient), octisalate, (emollient/UV filter), silicone fluid (emollient/diluent), squalene (emollient), sunflower oil (emollient), and silicone dioxide (thickening agent).

In one embodiment, lauryl lactate (for example, at about 0.1-10%, or about 0.2-5%, or about 0.5-5%) is included in the topical gel formulation. Lauryl lactate is considered safe for topical administration. Lauryl lactate is qualified for human use within pharmaceutical and cosmetic products. Lauryl lactate when used in a topical formulation enhances the permeability of the compound. Preferably lauryl lactate is purified to achieve >90%, preferably >95% purity; the high purity mitigates the presence of hydrolytic and oxidative agents. In addition, DMSO at 0.1-20%, or 0.5-10% (w/w) in the formulation provides suitable solubility of the active compound.

In another embodiment, diethylene glycol monoethyl ether is included in the topical gel formulation.

Method of Use

Inflammation is a process and a state of tissue pathology resulting from activation and continuation of activity of the innate and acquired components of the immune system. The arachidonic acid cascade and cytokine production and action in cell to cell interactions are critical components of immune activation and response, which lead to inflammation. Arachidonic acid is a component of membrane phospholipids. After it is freed from phospholipids, arachidonic acid acts as a precursor to many of the known eicosanoids including prostaglandins and leucotrienes, which are known pro-inflammatory entities.

The active compound is effective in inhibiting pro-inflammatory cytokine release (e.g., IL-1β, IL-6, TNFα, IL-4 and IFNγ) from human peripheral blood mononuclear cells in vitro. The active compound is anti-inflammatory when applied topically in the mouse ear swelling model, in which the inflammation is induced by arachidonic acid.

The present invention is directed to a method of treating inflammation and/or pain. ω-(Methanesulfonyl)alkenylnitrile, can be used as is, or it can be administered in the form of a pharmaceutical composition that additionally contains a pharmaceutically acceptable carrier. The method comprises the steps of first identifying a subject suffering from inflammation and/or pain, and administering to the subject the active compound, in an amount effective to treat inflammation and/or pain. "An effective amount," as used herein, is the amount effective to treat a disease by ameliorating the pathological condition or reducing the symptoms of the disease.

In one embodiment, the method reduces or alleviates the symptoms associated with inflammation. The present invention provides a method to treat localized manifestation of inflammation characterized by acute or chronic swelling, pain, redness, increased temperature, or loss of function in some cases.

In another embodiment, the present invention provides a method to alleviate the symptoms of pain regardless of the cause of the pain. The general term "pain" treatable by the present method includes nociceptive, neuropathic, and mix-type. The present invention reduces pain of varying severity, i.e. mild, moderate and severe pain; acute and chronic pain. The present invention is effective in treating joint pain, muscle pain, tendon pain, burn pain, and pain caused by inflammation such as rheumatoid arthritis.

In one embodiment, the present invention is useful in treating inflammation and/or pain associated in a musculoskeletal system. The highly innervated, musculoskeletal system has a high capacity for demonstration of pain. In addition, the musculoskeletal system has a high capacity for tissue swelling. In musculoskeletal system, the degree of tissue damage is frequently magnified out of proportion to the resulting inflammatory response.

The present invention provides a method for treating inflammation and/or pain associated with inflammatory skeletal or muscular diseases or conditions. The method comprises the steps of identifying a subject in need thereof, and administering to the subject the active compound, in an amount effective to treat inflammation and/or pain. "The active compound," as used herein, is intended to include the ω-(methanesulfonyl)alkenylnitrile compound (cis-isomer, trans-isomer, or a mixture thereof) and its pharmaceutically acceptable salts or solvate thereof. The skeletal or muscular diseases or conditions include musculoskeletal sprains, musculoskeletal strains, tendonopathy, peripheral radiculopathy, osteoarthritis, joint degenerative disease, polymyalgia rheumatica, juvenile arthritis, gout, ankylosing spondylitis, psoriatic arthritis, systemic lupus erythematosus, costochondritis, tendonitis, bursitis, such as the common lateral epicondylitis (tennis elbow), medial epicondylitis (pitchers elbow) and trochanteric bursitis, temporomandibular joint syndrome, and fibromyalgia.

In one embodiment, the present invention provides a method for treating inflammation and/or pain associated with joints, ligaments, tendons, bone, muscles, or fascia. The method comprises the steps of administering to a subject in need thereof the active compound, in an amount effective to treat inflammation and/or pain.

The present invention also provides a method for treating pain by the combined administration of morphine and methanesulfonylacrylonitrile. The method comprises the steps of: identifying a subject suffering from pain, and administering to the subject an effective amount of morphine and an effect amount of methanesulfonylacrylonitrile. The combined treatment can reduce the dosage of each single drug and can increase the analgesic effects. In the combined treatment, morphine and methanesulfonylacrylonitrile can be simultaneously or sequentially administered. For simultaneous administration, morphine and methanesulfonylacrylonitrile can be pre-mixed in one single formulation before administration. Alternatively, morphine and methanesulfonylacrylonitrile can be separately administrated.

The present invention further provides a method for potentiating the analgesic effect of morphine. The method comprises administering an effect amount of ω-methanesulfonylacrylonitrile to a subject who suffers from pain and is being treated with morphine. The administration of ω-methanesulfonylacrylonitrile increases the analgesic effect of morphine, and thus less morphine can be used to achieve an optimal analgesic effect. In addition, the analgesic effect is prolonged.

In one embodiment, the present invention is directed to a method of treating inflammation and/or pain associated gout. Gout is a chronic inflammatory disease that is characterized by recurrent, sudden, and severe attacks of acute inflammation (redness and tenderness) and pain at the joints, often at the base of the big toe. Gout is caused by elevated levels of uric acid in the blood. Gout is a type of arthritis. Some people may develop chronic gout, which is also called gouty arthritis.

Skin is highly reactive to environmental stimuli and the epidermal component of keratinocytes is a very rich source of both arachidonic acid and pro-inflammatory cytokines of IL-1 and TNF. The skin dendritic cells, Langerhans cells, recognize and process antigens for further immune response of various lymphocytes and all of these cells are primarily regulated by cytokines through their specific cell surface receptors.

ω-(methanesulfonyl)alkenylnitriles, which are effective in inhibiting arachidonic acid induced inflammation and in inhibiting the release of pro-inflammatory cytokine, are effective to treat inflammation and/or pain associated with inflammatory skin diseases such as psoriasis, acne, rosacea, and dermatitis (e.g., contact dermatitis, and atopic dermatitis).

ω-(Methanesulfonyl)alkenylnitrile, which are effective in inhibiting arachidonic acid induced inflammation and in inhibiting the release of pro-inflammatory cytokine, are effective to treat inflammatory skin diseases such as dermatitis (atopic dermatitis), psoriasis, acne, and rosacea.

The present invention provides a method for treating inflammation and/or pain associated with inflammatory skin diseases such as psoriasis, acne, rosacea, and dermatitis, particularly contact dermatitis, and atopic dermatitis. The method comprises the steps of identifying a subject in need thereof, and administering to the subject an ω-(methanesulfonyl)alkenylnitrile, in an amount effective to treat inflammation and/or pain.

The present invention further provides a method for treating inflammatory skin diseases such as dermatitis, psoriasis, and acne (Acne vulgaris). The method comprises the steps of identifying a subject in need thereof, and administering to the subject an ω-(methanesulfonyl)alkenylnitrile, in an amount effective to reduce or eliminate the symptoms of the disease.

Dermatitis (also called eczema) is generic inflammation of the skin. Specific types of dermatitis include atopic, contact, nummular, and photo-induced.

Contact dermatitis is a localized rash or irritation of the skin caused by contact with a foreign substance. Only the superficial regions of the skin are affected in contact dermatitis. Inflammation of the affected tissue is present in the epidermis (the outermost layer of skin) and the outer dermis (the layer beneath the epidermis). Contact dermatitis results in large, burning, and itchy rashes. Contact dermatitis is an inflammatory condition of the skin either of irritant exposure to the skin without specific adaptive immunologic pathogenesis or of allergic sensitization and subsequent exposure of the skin to the sensitizing allergen with specific adaptive immunologic pathogenesis. Both involve innate and acquired immune system response including arachidonic acid and cytokine components that initiate and propagate the disease through cell to cell messaging by eicosanoid and/or cytokine moieties produced by epidermal cells, macrophages, dendritic cells, neutrophils, eosinophils, and various T and B lymphocytes. Contact dermatitis may be either acute or chronic. The acute forms are pruritic with erythema, edema, and micro or macrovesiculation in the areas of skin contact by the initiating factor. The chronic forms are pruritic with milder erythema, scaling, lichenification, and possibly fissuring particularly on the hands.

Allergic contact dermatitis is a T cell-mediated delayed type hypersensitivity reaction that occurs upon hapten challenge in sensitized individuals. The inflammatory response in classical allergic contact dermatitis requires both a sensitization phase and an elicitation phase responsible for the recruitment and activation of specific T cells at the site of hapten skin challenge.

Atopic dermatitis is a genetically determined disease that is part of the broader disease complex of atopy that includes asthma, hay fever, and atopic dermatitis. Many individuals with atopic dermatitis have various mutations of the filaggrin gene that codes for an important epidermal structural protein that when defective, results in abnormal barrier function of the epidermis. The altered barrier allows exposure to multiple environmental allergens that are first recognized by innate immune responses involving arachidonic acid and eicosanoids and recruitment of eosinophils, mast cells, and other inflammatory cells that initiate an acute responses of itch, erythema, and subsequent scratching and additionally activate the adaptive immune responses that involve inflammation by lymphocytes predominantly of a TH 2 derivation and activity. Atopic dermatitis is responsive to a number of cytokine inhibitors such as cyclosporine, and tacrolimus.

Current theory of the pathogenesis of psoriasis is that in individuals who are genetically susceptible a triggering event in the epidermis such as injury or super antigen contact initiates an response of the innate immune system with arachidonic acid and eicosanoid generation, recruitment and activity of neutrophils. Subsequent transformation of the response to that of a TH 1 adaptive immunity with cytokine activation and activity of specific T lymphocytes effect the pathological changes in the epidermis and dermis, which result in the typical psoriasis lesions of plaques that are erythematous, thickened, and scaly. Psoriasis is responsive to various immunomodulators including cyclosporine, methotrexate, and a host of specific biologicals that interfere with cytokine signaling.

Acne vulgaris, a progressively inflammatory disorder of the pilosebaceous follicular unit especially of the face and upper chest and back is a very common disease of both males and females after initiation of puberty, and in females even prior to adrenal gland maturity. Increased production of androgenic hormones by adrenal, ovarian, and testicular glands and by the pilosebaceous unit itself produce an increase in sebum and changes in its lipid composition, which combine with follicular epithelial cells to produce some degree of obstruction of the infra-infundibular portion of the pilosebaceous follicle resulting in the initial lesion of acne, the microcomedo. This consequent dilation of the pore and the changed composition of sebum at puberty facilitate colonization of the follicle by *Propionibacterium acnes* bacilli that produce enzymes to degrade the triglycerides in sebum to free fatty acids that leak through the follicle into the dermis and incite arachidonic acid pathways of eicosanoid production and subsequent initiation of inflammation. The bacilli also initiate chemokine production that attracts further inflammatory cells to the area and consequent cytokine production and action to continue and amplify inflammation. Thus initiation and propagation of progressive inflammation in the microcomedo produces the evolution to the several hallmark lesions of inflammatory acne, papule, pustule, nodule, and cyst. The present invention is useful to treat common acne, comedonic acne, papulopustular acne, papulocomedonic acne, nodulocystic acne, acne conglobata, cheloid acne of the nape of the neck, recurrent miliary acne, necrotic acne, neonatal acne, occupational acne, acne rosacea, senile acne, solar acne or acne medicamentosa.

Rosacea is a chronic condition characterized by facial erythema and sometimes pimples. Rosacea typically begins as redness on the central face across the cheeks, nose, or forehead, but can also less commonly affect the neck, chest, ears, and scalp. In some cases, additional symptoms, such as semi-permanent redness, telangiectasia (dilation of superficial blood vessels on the face), red domed papules (small bumps) and pustules, red gritty eyes, burning and stinging sensations, and in some advanced cases, a red lobulated nose (rhinophyma), may develop. There are 3 subtypes of rosacea that affect the skin: erythematotelangiectatic rosacea, papulopustular rosacea, and phymatous rosacea.

ω-(Methanesulfonyl)alkenylnitriles are effective in treating atopic dermatitis and alleviating one or more symptoms selected from the group consisting of erythema, induration, lichenification, scaling, and oozing and crusting.

ω-(Methanesulfonyl)alkenylnitriles are effective in treating psoriasis and alleviating erythema, scaling, and/or thickness of the psoriasis lesions.

ω-(Methanesulfonyl)alkenylnitriles are effective in treating acne and alleviating acne lesions selected from the groups consisting of closed comedones, papules, pustules, nodules, and cysts.

ω-(Methanesulfonyl)alkenylnitriles are effective in treating rosacea and alleviating one or more symptoms selected from the group consisting of erythema, telangiectasia, red domed papules and pustules, red gritty eyes, and burning and stinging sensations.

The pharmaceutical composition of the present invention can be applied by local administration and systemic administration. Local administration includes topical administration. Systemic administration includes oral, parenteral (such as intravenous, intramuscular, subcutaneous or rectal), and other systemic routes of administration. In systemic administration, the active compound first reaches plasma and then distributes into target tissues. Topical administration and oral administration are preferred routes of administration for the present invention.

Dosing of the composition can vary based on the extent of the injury and each patient's individual response. For systemic administration, plasma concentrations of the active compound delivered can vary; but are generally $1\times10^{-10}$-$1\times10^{-4}$ moles/liter, and preferably $1\times10^{-8}$-$1\times10^{-5}$ moles/liter.

In one embodiment, the composition is applied topically onto the affected area and rubbed into it. The composition is topically applied at least 1 or 2 times a day, or 3 to 4 times per day, depending on the medical issue and the disease pathology being chronic or acute. In general, the topical composition comprises about 0.01-20%, or 0.05-20%, or 0.1-20%, or 0.2-15%, 0.5-10, or 1-5% (w/w) of the active compound. For example, the topical composition comprises about 1 or 5% (w/w) of the active compound. Depending on the size of the affected area, 0.2-85 mL, typically 0.2-10 mL, of the topical composition is applied to the individual per dose. The active compound passes through skin and is delivered to the site of discomfort.

In one embodiment, the pharmaceutical composition is administrated orally to the subject. The dosage for oral administration is generally 0.1-20 mg/kg/day. For example, the dosage for oral administration is 0.1-10, 0.5-10, or 1-10 mg/kg/day, for a human subject. For example, the dosage for oral administration is 1-600 mg/day, and preferably 1-100, 10-50 mg/day for a human subject.

In one embodiment, the pharmaceutical composition is administrated intravenously to the subject. The dosage for intravenous bolus injection or intravenous infusion is generally 0.03 to 5 or 0.03 to 1 mg/kg/day.

In one embodiment, the pharmaceutical composition is administrated subcutaneously to the subject. The dosage for subcutaneous administration is generally 0.3-20, 0.3-3, or 0.1-1 mg/kg/day.

Those of skill in the art will recognize that a wide variety of delivery mechanisms are also suitable for the present invention.

The present invention is useful in treating a mammal subject, such as humans, horses, and dogs. The present invention is particularly useful in treating humans.

The following examples further illustrate the present invention. These examples are intended merely to be illustrative of the present invention and are not to be construed as being limiting.

EXAMPLES

Example 1. Preparation of 3-(methylsulfonyl)acrylonitrile

A methanolic solution of 2,3-dichloropropionitrile (60 mmol, a) was added dropwise to a mixture of sodium methanesulfinate (1 equivalent) in aqueous methanol containing sodium acetate (2 equivalent). The reaction was monitored by TLC. After being stirred for about 1.5 hours, the reaction mixture was diluted with water and extracted with $CHCl_3$. The $CHCl_3$ extract was washed with water, treated with charcoal and concentrated. The residue was crystallized from hot ethanol. The yield of 3-(methylsulfonyl)acrylonitrile (b) was 1.12 g (14%).

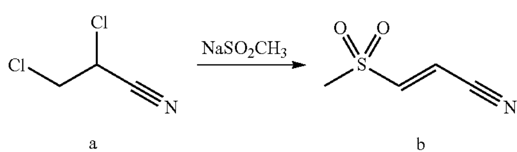

The product had a white, crystalline appearance. The melting point was 106.5-107.5° C. The results of FTIR-ATR, $^1$HNMR, $^{13}$C NMR analyses were consistent the structure of b. The elemental analysis found C, 36.57, H, 3.84, and N, 10.70. The GC-MS study showed m/z of 132.

Example 2. Gel Formulation 1

Table 1 exemplifies one gel formulation containing ω-(methanesulfonyl)alkenylnitriles such as 3-(methylsulfonyl)acrylonitrile.

TABLE 1

| | 1% Gel |
|---|---|
| Active compound | 1.0% |
| Dow Corning Elastomer Blend EL-8050 ID | 69.0% |
| Labrafac Lipophile WL 1349 | 8.0% |
| Octisalate | 5.0% |
| Lauryl Lactate | 3.2% |
| Dimethyl Sulfoxide (DMSO) | 1.8% |
| Dow Corning 556 Cosmetic Grade Fluid | 7.9% |
| Squalene | 2.0% |
| Sunflower Seed Oil | 2.0% |
| Dow Corning Aerogel VM-2270 | 0.0% |
| Total | 100.0% |

Example 3. Gel Formulation 2

Table 2 exemplifies another gel formulation containing ω-(methanesulfonyl)alkenylnitriles such as 3-(methylsulfonyl)acrylonitrile.

TABLE 2

| | 1-5% Gel |
|---|---|
| Active compound | 1.0-5.0% |
| Diethylene glycol monoethyl ether | 5.0% |
| Acrylates/C10-30 alkyl acrylate crosspolymer (CARBOPOL ® Ultrez 20 polymer) | 0.50% |
| Trolamine (tris(2-hydroxyethyl)amine) | 0.47% |
| Purified Water | 89.03-93.03% |
| Total | 100.0% |

Example 4. In Vitro Inhibition of Cytokine Activities by 3-(methylsulfonyl)acrylonitrile Objective: Test 3-(methylsulfonyl)acrylonitrile for inhibition of cytokine secretion in peripheral blood mononuclear cells (PBMCs) stimulated with lipopolysaccharide (LPS).
Cytokines: IL-1β, IL-6, TNFα
Test Compound Dose Concentrations: 50, 10, 5, 1, 0.5, 0.1 μM
Controls
Vehicle: DMSO, 0.1% v/v
LPS control: LPS+Vehicle
Cells negative control: Vehicle only/No LPS
Positive control: Dexamethasone (100 nM, n=2)
Protocols
1. Microtiter plates were seeded with $1\times10^4$ PBMCs/well in 1504, culture medium (RPMI 1640, 10% FBS, 1% Pen/Strep, 2 mM L-Alanyl-L-glutamine)
2. The plates were incubated at 37° C. in 5% $CO_2$ for 1 hour.
3. 10 μL of test compound (at different concentrations), dexamethasone, and vehicle controls were added to appropriate wells, and the plates were incubated at 37° C. in 5% $CO_2$ for 1 hour.

4. 40 μL of LPS (50 pg/mL final) were added and the plates were incubated at 37° C. in 5% $CO_2$ for 1 hour.
5. The plates were centrifuged at 1000 rpm for 10 minutes and supernatants were collected.
6. The supernatants were assayed for IL-1β, IL-6, TNFα levels using the Luminex Bead kit.
7. EC50 values were determined.

Results

The EC50's of 3-(methylsulfonyl)acrylonitrile for inhibiting IL-1β, IL-6, and TNFα were 0.16 μM, 0.19 μM, and 0.30 μM respectively. The results demonstrate that the active compound has an inhibitory effect on cytokines involved in the inflammatory process.

Example 5. Anti-inflammatory Activity of Oral Administration of 3-(methylsulfonyl)acrylonitrile in Mice 3-(Methylsulfonyl)acrylonitrile was suspended in vehicle (1% Tween 80 in water) to 0.1-2 mg/mL. The test compound, dexamethasone (positive control), and vehicle were orally administered to mice and evaluated for anti-inflammatory activity in the topical arachidonic acid induced ear swelling model in mice.

Male ICR derived mice weighing 22±2 g were used in this experiment. 5 mice were used for each group (active compound, positive control, and vehicle). All animals were maintained in a controlled temperature (22-24° C.) and humidity (60%-70%) environment with 12-hour light/dark cycles for at least one week prior to use.

Arachidonic acid (0.5 mg in 20 μL acetone) was applied topically onto the anterior and posterior surfaces of the right ear of test animals to induce inflammation. Active compound of different concentrations in vehicle (10 mL/kg) and vehicle (10 mL/kg) were orally administered by gavage 1 hour before arachidonic acid, whereas dexamethasone (0.3 mg/kg) was orally administered by gavage 3 hour before arachidonic acid challenge. At 60 minutes after arachidonic acid induction of ear edema, the thickness of the right ear and the left ear was measured and the difference calculated as an indication of the inflammation in the right ear. Significant activity was defined as a statistically significant inhibition (p-value determined by t-test was <0.05) in arachidonic acid induced ear swelling relative to the vehicle-treated group. The results are shown in Table 3. Oral administration of 3-(methylsulfonyl)acrylonitrile at dosage of 10 mg/kg caused significant inhibition in arachidonic acid induced ear swelling at 60 minutes.

TABLE 3

| Test Substance | Dosage mg/kg | % Inhibition | P Value |
|---|---|---|---|
| Vehicle (1% Tween 80 in water) | NA | NA | |
| Dexamethasone (Positive control) | 0.3 | 39 | <0.005 |
| Test Compound | 0.1 | 11 | 0.364 |
| Test Compound | 0.3 | 11 | 0.364 |
| Test Compound | 1 | 9 | 0.397 |
| Test Compound | 3 | 13 | 0.172 |
| Test Compound | 10 | 26 | 0.042 |

Example 6. Potentiation of Analgesic Activity of Morphine by 3-(methylsulfonyl)acrylonitrile in Mice Nociceptive Assays The response of the mice to nociceptive stimuli was evaluated using the time of tail-flick or tail-flick latency from 52° C. water bath. Briefly, the animal was placed in a restrainer with its tail outside. The tail (distal ⅓rd) was immersed into 52° C. water and the time for the mouse to flick its tail out of the water was recorded. The maximum exposure permitted was 10 seconds. If there was no response within 10 seconds, the animal tail was removed from the water to prevent damage to the tail. Baseline data were collected using the tail flick procedure 2 times over 1 hour, prior to any drug administration. The last baseline response data point was used as basal tail flick latency.

Drug Treatments 3-(methylsulfonyl)acrylonitrile was dissolved in 0.5% methyl cellulose (MC) to 2 mg/mL, and orally administered to mice (n=5) in a volume of 10 ml/kg (20 mg/kg), 1 hour prior to morphine dosing. One mL plastic disposal tuberculin syringes (Becton Dickinson & Co. Franklin Lakes, N.J.) and 20 gauge×38 mm flexible plastic feeding tubes (Instech Laboratories, Plymouth Meeting, Pa.) were used for oral drug administration. Morphine at 5 mg/kg in saline was subcutaneously administered to mice at time zero.

Tail flick measurements were made at 5, 15, 30, 45, 60, and 75 minutes post-morphine administration.

Data Analysis

Statistical evaluation was done using an appropriate analysis of variance (ANOVA) using tail flick latencies. Results of tail flick response from each group are calculated as mean+/−standard error of mean. Analysis with p-values <0.05 is considered significant.

Results

The results are shown in FIG. 1. Comparing the latency of mice tail flick between morphine alone and morphine plus 3-methanesulfonylacrylonitrile, the administration of 3-methanesulfonylacrylonitrile increases the latency of tail flick significantly when measured at 30, 60, and 75 minutes post morphine dosing. The p values between morphine alone and morphine plus methanesulfonylacrylonitrile at 30, 60, and 75 minutes post morphine dosing are 0.0033, 0.473, and 0.0045, respectively. Further, the results show that morphine alone had no effect at 75 minutes post dosing, whereas morphine plus methanesulfonylacrylonitrile still had a strong analgesic effects at 75 minutes post dosing.

Example 7. Anti-Inflammatory and Analgesic Activity of the Active Compound by Oral Administration in a Carrageenan Model (Prophetic Example)

Active compounds of ω-(methanesulfonyl)alkenylnitrile such as 3-(methylsulfonyl)acrylonitrile are suspended in vehicle (1% Tween 80 in water) to 0.5-2 mg/mL. Active compounds, indomethacin (positive control), and vehicle (1% Tween 80 in water) are orally administered and evaluated for anti-inflammatory and analgesic activity in the rat carrageenan-induced paw inflammation model.

Rats are used in the experiment. Carrageenan (0.1 mL of a 1% suspension) is injected subcutaneously into the left hind paw to induce inflammation. Active compounds in vehicle (10 mL/kg) and vehicle are orally administered 1-2 hours before the carrageenan administration. Indomethacin is given orally at 5 mg/kg, 1 hour prior to carrageenan administration. The degree of inflammation (edema, or swelling) is determined using a plethysmograph to measure paw volume. Analgesia is determined by measuring paw withdrawal to a mechanical stimulus using von Frey filaments. Inflammation and analgesia are measured 4 hours after carrageenan administration. ω-(methanesulfonyl)alkenylnitriles are expected to have anti-inflammatory and/or analgesic properties as measured by a significant decrease in paw volume and/or a significant increase in mechanical pressure needed to elicit paw withdrawal, respectively, as compared to the vehicle control.

Example 8. Anti-Inflammatory and Analgesic Activity of Active Compound by Topical Administration in a Carrageenan Model (Prophetic Example)

Active compounds of ω-(methanesulfonyl)alkenylnitrile such as 3-(methylsulfonyl)acrylonitrile are prepared in the gel formulation according to Example 2 or 3.

Test materials in gel formulation (1-5%), indomethacin (positive control), and vehicle (gel formulation without active compound), are evaluated for anti-inflammatory and analgesic activity in the rat carrageenan-induced paw inflammation model.

Rats are used in the experiment. Carrageenan (0.1 mL of a 1% suspension) is injected subcutaneously into the left hind paw to induce inflammation. Test material (1-5%) or vehicle gel is applied to the paw topically at volumes of 0.05, 0.1 0.15 or 2.0 mL, 1.5, 2.5, and 3.5 hours following the carrageenan administration. Indomethacin is given orally at 5 mg/kg, 1 hour prior to carrageenan administration. The degree of inflammation (edema, or swelling) is determined using a plethysmograph to measure paw volume. Analgesia is determined by measuring paw withdrawal to a mechanical stimulus using von Frey filaments. Inflammation and analgesia are measured 4 hours after carrageenan administration. Test materials are expected to have anti-inflammatory and/or analgesic properties as measured by a significant decrease in paw volume and/or a significant increase in mechanical pressure needed to elicit paw withdrawal, respectively, as compared to the vehicle control.

Example 9. Analgesic Activity of the Active Compound by Oral Administration in a Hot Plate Model (Prophetic Example)

Active compounds of ω-(methanesulfonyl)alkenylnitrile such as 3-(methylsulfonyl)acrylonitrile are suspended in vehicle (1% Tween 80 in water) to 0.5-2 mg/mL. Active compound, morphine (positive control), and vehicle (1% Tween 80 in water) are orally administered and evaluated for analgesic activity in the rat hot plate model.

Rats are used in the experiment. Active compounds in vehicle (10 mL/kg) and vehicle (1% Tween 80 in water) are orally administered 1-2 hours before the rat is placed on a 55° C. hot plate, and the time to lick the paw is measured. The positive control, morphine, is given orally at 30 mg/kg, 1 hour prior to hot plate testing. ω-(Methanesulfonyl)alkenylnitriles are expected to have analgesic properties as measured by a significant increase in time to licking as compared to the vehicle control (t-test, $p<0.05$).

Example 10. Analgesic Activity of Active Compound in a Hot Plate Model by Topical Administration (Prophetic Example)

Active compounds of ω-(methanesulfonyl)alkenylnitrile such as 3-(methylsulfonyl)acrylonitrile are prepared in the gel formulation according to Example 2 or 3.

Test materials: active compound in gel formulation (1-5%), morphine (positive control), and vehicle (gel formulation without active compound), are evaluated for analgesic activity in the rat hot plate model.

Rats are used in the experiment. Test material (1-5%) or vehicle gel is applied to the paw topically at volumes of 0.05, 0.1 0.15 or 2.0 mL. One hour later the rat is placed on a 55° C. hot plate, and the time to lick the paw is measured. The positive control, morphine, is given orally at 30 mg/kg, 1 hour prior to hot plate testing. Test materials are expected to have analgesic properties as measured by a significant increase in time to licking as compared to the vehicle control (t-test, $p<0.05$).

Example 11. Analgesic Activity of Active Compound in CFA-Induced Thermal Hyperalgesia by Oral or Topical Administration (Prophetic Example)

CFA (Complete Freund's Adjuvant) is known to induce inflammatory pain. (Walker, et al. JPET. 304: 56-62, 2003.)

Male Sprague-Dawley rats weighing 180±20 g are used. The animals, divided into groups of 8-10 each, receive a subplantar injection (0.1 ml) of CFA (0.1% solution) to the tested hindpaw at 24 hours prior to experimentation. Thermal hyperalgesia is tested by using the IITC Model-336G (IITC INC. USA) apparatus with a thermally regulated glass floors set at 30° C. Each rat is placed within a plastic box atop a glass floor. A light beam under the floor is aimed at the plantar surface of the right hind paw. The time is measured automatically when the paw is withdrawn away from the thermal stimulus. The intensity of the light is adjusted with average group baseline latency from 12 to 14 sec (pre-CFA) and a cut-off latency of 20 sec imposed. The latency to withdrawal is obtained for each rat and defined as the heat pain threshold. Twenty four hours after CFA injection, rats are pre-selected (with clear presence of thermal hyperalgesia) for experimentation only if the latency to withdrawal is less than 75% of baseline.

Active compounds of ω-(methanesulfonyl)alkenylnitrile such as 3-(methylsulfonyl)acrylonitrile are prepared in the gel formulation according to Example 2 or 3.

Active compound in gel formulation (1-5%), active compound in oral vehicle, morphine (positive control, p.o., 20 mg/kg), topical vehicle (gel formulation without an active compound), and oral vehicle (1% Tween 80 in water) are evaluated for analgesic activity in the formalin model.

Test substance or vehicle is either administered orally (10-20 mg/kg) or topically (1-5% gel formulation) to the plantar surface of the hind paw, at 60 minutes before the level of thermal hyperalgesia is again measured (post-treatment). Mean±SEM of thermal paw withdrawal time is calculated. Unpaired Student's t test is applied for comparison the values of post-treatment between test substance treated group and vehicle control group. Positive activity is considered at $P<0.05$.

Example 12. Analgesic Activity of Active Compound in a Formalin Test by Oral or Topical Administration (Prophetic Example)

Formalin test is a model of continuous pain resulting from formalin-induced tissue injury. The formalin model encompasses inflammatory, neurogenic, and central mechanism of nociception. The assay described below relates primarily to the late inflammatory analgesic phase sensitive to both strong central analgesic as well as weaker analgesic/anti-inflammatory agents (Hunskaar, et al., J. Neuroscience Meth. 14: 69-76, 1985). The formalin test represents a suitable model for testing compounds for treating neuropathic pain (Benson, et al. Proceedings of Measuring Behavior, 2008, Eds. Spink, et al, 324-325).

Active compounds of ω-(methanesulfonyl)alkenylnitrile such as 3-(methylsulfonyl)acrylonitrile are prepared in the gel formulation according to Example 3.

Active compound in gel formulation (1-5%), active compound in oral vehicle, morphine (positive control, p.o., 30 mg/kg), topical vehicle (gel formulation without an active compound), and oral vehicle (1% Tween 80 in water) are evaluated for analgesic activity in the formalin model.

Test substance is administered to groups of 8-10 CD-1 derived male mice weighing 23±3 g one hour before subplantar injection of formalin (0.02 ml, 2% solution). Test substance is either administered orally (10-20 mg/kg) or topically (1-5% gel formulation) to the plantar surface of the hind paw. Reduction of the induced hind paw licking time recorded during the following 10 to 30 minute period by 50% or more indicates analgesic activity. Positive activity is considered by a significant increase in time to licking in test compound as compared to the vehicle control (t-test, $p<0.05$).

Example 13. Analgesic Activity of Active Compound in Chronic Constriction Injury Model by Oral or Topical Administration (Prophetic Example)

Peripheral nerve lesions may generate a syndrome comprising, in addition to spontaneous pain, exaggerated responses to light touch (tactile allodynia). Chronic constriction injury model is a neuropathic pain model.

Male Sprague Dawley rats weighing 180±20 g are used. Under pentobarbital (50 mg/kg, 5 ml/kg, i.p.) anesthesia, the sciatic nerve is exposed at mid-thigh level. Four ligatures (4-0 chromic gut), about 1 mm apart, are loosely tied around the nerve. The animals are then housed individually in cages with soft bedding for 7 days before testing. Constriction of the sciatic nerve produces nerve injury and unilateral neuropathic pain.

On the day of experiments, the animals have no access to food overnight before testing. The rats are placed under inverted plexiglass cages on a wire mesh rack and allowed to acclimate for 20 to 30 minutes. Mechanic allodynia is evaluated by the Chaplan up/down method using von Frey filaments to the plantar surface of the left hind paw. See Chaplan, et al. J. Neuroscience Methods, 53: 55-63, 1994.

Rats are pre-selected for experimentation only if the pain threshold 7-14 days after nerve ligation (pre-treatment) is reduced by 10 grams of force relative to the response of the individual paw before nerve ligation (pre-ligation), namely, with clear presence of allodynia.

Active compounds of ω-(methanesulfonyl)alkenylnitrile such as 3-(methylsulfonyl)acrylonitrile are prepared in the gel formulation according to Example 3.

Active compound in gel formulation (1-5%), active compound in oral vehicle, morphine (positive control, p.o., 20 mg/kg), topical vehicle (gel formulation without an active compound), and oral vehicle (1% Tween 80 in water) are evaluated.

Test substance or vehicle is either administered orally (10-20 mg/kg) or topically (1-5% gel formulation) to the plantar surface of the left hind paw. The mechanical allodynia test is performed 30 min before (pre-treatment) and 1 and 3 hours after a single dose of test substance or vehicle (post treatment). Paw withdraw thresholds of control and tested compound are measured.

Example 14. Treatment of Arthritis (Prophetic Example)

Zymosan injected directly into the knee joint of mice elicits an inflammatory response and is used as a model of arthritis (Verschure et al, Ann. Rheum Dis. 53:455-460, 1994).

Endpoints measured in this model include knee joint swelling score, cytokine levels in the synovial tissue and microscopic pathology of the knee.

Active compound 3-(methylsulfonyl)acrylonitrile (10-20 mg/kg in water, oral application) and vehicle control (water) are administered by oral gavage to mice with a volume of 5 mL/kg.

There are 5 mice per group, with a total of 10 knees injected. On Day 1, C57BL6 mice are dosed (30 or 100 mg/kg/dose) with active compound or vehicle twice on Hours 0 and 12. On Day 2, mice are dosed with active compound or vehicle on Hour 24, then injected intra-articularly with 180 μg of zymosan (6 μL) into both knee joints on Hour 25, and then dosed a second time on Hour 36 with each active compound or vehicle. On Day 3, mice are again dosed with active compound or vehicle on Hour 48. Two hour post-dosing on Hour 50, knees are scored for edema, synovial tissue is collected for measurement of cytokine levels, and knee joints are processed for histopathology for analysis of inflammatory immune cell influx into the joint. Macroscopic joint swelling is assessed on all knees after the skin is removed using a scoring system ranging from 0 to 3, with 0 being no swelling and 3 being severe swelling. Synovial tissue is taken from 5 knees for measurement of mouse interleukin-1β, interleukin-6, and interleukin-1 receptor antagonist levels. The remaining 5 knees are processed for microscopic pathology for assessment of cellular influx into the site of inflammation.

Results for each group are presented as mean±standard error of mean and statistical evaluation is performed.

Treatment with active compound is expected to result in decreased inflammation as measured by a decrease in joint swelling, decrease in cytokine levels and decrease influx of inflammatory cells to the site of inflammation.

Example 15. Treatment of Gout (Prophetic Example)

Monosodium urate monohydrate (MSU) crystals injected in combination with a free fatty acid (FFA) directly into the knee joint of mice elicits an inflammatory response and is used as a model of gout (Joosten et al, Arthritis & Rheumatism, 62(11):3237-3248, 2010)). Endpoints measured in this model include knee joint swelling score, cytokine levels in the synovial tissue and microscopic pathology of the knee.

Active compound 3-(methylsulfonyl)acrylonitrile (2-4 mg/mL in water, oral application) and vehicle control (water) are administered by oral gavage to mice with a volume of 5 mL/kg.

There are 5 mice per group, with a total of 10 knees injected. On Day 1, C57BL6 mice are dosed (50, 200, or 500 mg/kg/dose) with active compounds or vehicle twice on Hours 0 and 12. On Day 2, mice are dosed with active compounds or vehicle on Hour 24, then injected intra-articularly with MSU crystals (300 μg) and C18:0 FFA (200 μM, 10 μL) on Hour 25. Three hours later (Hour 28), knees are scored for edema, synovial tissue is collected for measurement of cytokine levels, and knee joints are processed for histopathology for analysis of inflammatory immune cell influx into the joint. Macroscopic joint swelling is assessed on all knees after the skin is removed using a scoring system ranging from 0 to 3, with 0 being no swelling and 3 being severe swelling. Synovial tissue is taken from 5 knees for measurement of mouse interleukin-1β, interleukin-6, and interleukin-1 receptor antagonist levels. The remaining 5 knees are processed for microscopic pathology for assessment of cellular influx into the site of inflammation.

Results for each group are presented as mean±standard error of mean and statistical evaluation is performed.

Treatment with active compound is expected to result in decreased inflammation as measured by a decrease in joint swelling, decrease in cytokine levels and decrease influx of inflammatory cells to the site of inflammation.

Example 16. Treatment of Knee Pain by Oral or Topical Administration (Prophetic Example)

Objectives:

To investigate the efficacy of the active compound in a gel formulation or in an oral formulation in patients with mild to moderate knee pain associated with osteoarthritis following temporary cessation of standard NSAID therapy. The focus of this study is on the symptoms caused by painful arthritis. The clinical trial is utilizing osteoarthritis of the knee as a well-established paradigm for other musculoskeletal disorders.

Topical Formulation:

The gel formulation containing the active compound 3-(methylsulfonyl)acrylonitrile at 1% and 5% (Example 3) are used in this example. Placebo contains the same gel without the active compound.

Oral Formulation:

Capsules or tablets each containing 50-200 mg of the active compound 3-(methylsulfonyl)acrylonitrile are used in this example. Placebo capsules or tablets do not contain the active compound.

Methodology:

A randomized, double-blind, placebo controlled, parallel treatment multicenter clinical activity study.

Patients with painful osteoarthritis of the knee, controlled by a stable dose of standard NSAID therapy for at least 2 months, discontinue use of the NSAIDs for a 7-day washout period. Patients are then randomized in a 1:1:1 ratio (1% active gel, 5% active gel, placebo). A total of up to 150 patients are enrolled and treated for 14 days with follow-up at 14, 21, and 28 days.

The active gel or placebo is applied to the affected knee 3 times a day for 14 days for a total of 42 treatments given every 4-6 hours while awake.

The capsules or tablets are orally administered to patients 1-4 times a day for 14 days.

Patients are treated for 14 days and followed up for a further 14 days. NSAIDs may be restarted after the Day 14 visit.

Criteria for Evaluation:

Safety:

Adverse Events (AEs) throughout the study.

Physical examination at enrollment (−7 days, start of NSAID washout period), Baseline, Day 14 and Day 28.

Vital signs at enrollment (−7 days, start of NSAID washout period), Baseline and Days 7, 14, 21, 28.

Clinical laboratory measurements at Baseline, and Days 7, 14, 21 and 28.

Clinical Activity:

The primary clinical activity parameters are the measurement of pain at the site of application, as quantified by Pain on Movement assessment (100-mm VAS) and the Western Ontario and McMaster University (WOMAC) index (100-mm VAS or 5-point Likert scale). The effect of treatment on swelling, tenderness and inflammation of the knee is recorded, also the time to reduction or eradication of pain after treatment is recorded.

Study Endpoints:

The primary clinical activity endpoints are:

Change from Baseline to Day 14 in WOMAC functional disability index and sub-indices:

Pain (Scale 0-20).

Stiffness (Scale 0-8).

Physical function (Scale 0-68).

Change from Baseline (Day 1) to Day 14 in Pain on Movement (1-100 mm VAS).

The secondary clinical activity endpoints are:

Change in Current Knee Pain score (100 mm VAS) at Baseline from pre-dose to 1 hour post-dose Change in Current Knee Pain score (100 mm VAS) at Baseline from pre-dose to 2 hours post-dose Change in Global Rating of Disease (5-point Likert scale)

Time to reduction or eradication of pain subsequent to each application of active compound.

Use of rescue medication (APAP).

Proportion of subjects experiencing an improvement in Pain on Movement (100-mm VAS) from Baseline to Day 14, equal to or greater than the minimum clinically important improvement (MCII) threshold of 15 mm or 20%

Proportion of subjects whose Pain on Movement (100-mm VAS) at Day 14 is less than the Patient Acceptable Symptom State (PASS) threshold of 40 mm Proportion of subjects who are 'Responders' based on the OARSI Responder Index, in relation to WOMAC Index.

Example 17. Treatment of Contact Dermatitis (Prophetic Example)

Mice dermally sensitized and challenged by dinitrofluorobenzene (DNFB) are used as a model of contact dermatitis (Saint-Mezard, J Invest Dermatol, 120:641-647, 2003).

Sensitization and Challenging:

There are 5 mice per group. Each mouse is sensitized with 0.5% DNFB (vehicle=4:1 (vol/vol) acetone:olive oil) topically on the shaved abdomen, 6 days before challenge. The right ears of the mice are then challenged with a topical application of 0.2% DNFB in vehicle. The left ears of the mice receive the vehicle as control.

Oral Administration:

Active compound 3-(methylsulfonyl)acrylonitrile (2-4 mg/mL in water) and control (water) are administered by oral gavage to mice with a volume of 5 mL/kg.

Before challenge, each group of mice receive oral dosages of active compound or water at 24 hours, 12 hours, and 2 hours before the challenge.

After challenge, the same oral dosages of active compound or water are given to each mouse 7 hours, 22 hours, 31 hours, 46 hours, and 55 hours after the challenge. The thickness of the left and right ears are measured before challenge, and 24, 48, and 72 hours after challenge. Results are expressed as net swelling: thickness after challenge minus thickness before challenge. Net swelling of treated mice vs. control mice are compared.

Topical Administration: Active compound (3-(methylsulfonyl)acrylonitrile prepared in vehicle (1:1; acetone:ethanol)

at 375 mM and vehicle alone are topically applied to both ears of the mice in a volume of 20 μl.

The topical doses are given after challenge to each mouse 7 hours, 22 hours, 31 hours, 46 hours, and 55 hours after the challenge. The thickness of the left and right ears are measured before challenge, and 24, 48, and 72 hours after challenge. Results are expressed as net swelling: thickness after challenge minus thickness before challenge. Net swelling of treated mice vs. control mice are compared.

Example 18. Treatment of Atopic Dermatitis (Prophetic Example)

Objectives:

To investigate the efficacy of 3-(methylsulfonyl)acrylonitrile gel in patients having atopic dermatitis.

Topical Formulation:

3-(methylsulfonyl)acrylonitrile is prepared as a gel formulation according to Example 3 or as a cream formulation according to Example 4. Active compounds in a gel or cream formulation are used in this experiment. Placebo contains the same gel or cream ingredients without the active compound.

Oral Formulation:

Capsules or tablets each containing 50-200 mg of the active compound 3-(methylsulfonyl)acrylonitrile are used in this example. Placebo capsules or tablets do not contain the active compound.

Methodology:

This is a randomized, double-blind, placebo controlled, parallel treatment clinical activity study.

Male and female patients with mild to severe atopic dermatitis are enrolled after discontinuation of all treatments for atopic dermatitis for a period of 4 weeks before study initiation. Patients are randomized in a 1:1 ratio (active gel, placebo). A total of 300 patients are enrolled and treated.

The active gel or placebo is applied twice a day to affected areas of the body for 12 weeks.

The capsules or tablets are orally administered to patients 1-4 times a day for 12 weeks. The treatment results are evaluated at 2 week intervals until week 12 and then at 4 weeks after discontinuation of the study medication.

Criteria for Evaluation:

Safety:

Safety is evaluated by general history and physical signs, laboratory testing for hematology, serum chemistry, and urinalysis, and by evaluations of local application site tolerability parameters of erythema, scaling, dryness, stinging/burning utilizing a rating scale of “0” (None) to “3” (Severe).

Efficacy:

Efficacy is evaluated utilizing:

1. an overall assessment of disease severity at study entry and at 2 week intervals until week 12 and subsequently at 4 weeks after study medication discontinuation. The investigator global assessment, IGA, is based upon a rating scale of 0 to 4 with 0=none or clear, 1=almost clear, 2=mild disease involvement, 3=moderate disease involvement, and 4=severe disease involvement, and:

2. separate evaluation of a representative target atopic dermatitis area of involvement for erythema, induration, lichenification, scaling, and oozing and crusting with each parameter rated on a 0-4 scale with 0=none or clear, 1=almost clear, 2=mild disease involvement, 3=moderate disease involvement, and 4=severe disease involvement.

Statistical analyses of each of these efficacy evaluations are performed for each of the 2 week study time points. Definitive evaluation of efficacy is based upon comparisons of active to vehicle groups at end of treatment at 12 weeks. The 4 week-post treatment evaluation is utilized to evaluate durability of treatment effect after medication discontinuation.

Example 19. Treatment of Psoriasis (Prophetic Example)

Objectives:

To investigate the efficacy of the 3-(methylsulfonyl)acrylonitrile gel in patients having psoriasis vulgaris.

Topical Formulation:

3-(methylsulfonyl)acrylonitrile is prepared as a gel formulation according to Example 3 or as a cream formulation according to Example 4. Active compounds in a gel or cream formulation are used in this experiment. Placebo contains the same gel or cream ingredients without the active compound.

Oral Formulation:

Capsules or tablets each containing 50-200 mg of the active compound 3-(methylsulfonyl)acrylonitrile are used in this example. Placebo capsules or tablets do not contain the active compound.

Methodology:

This is a randomized, double-blind, placebo controlled, parallel treatment clinical activity study.

Male and female patients with mild to severe psoriasis vulgaris are enrolled. Patients discontinue all treatments for psoriasis for a period of 4 weeks before study initiation. Patients are randomized in a 1:1 ratio (active gel, placebo). A total of 200 patients are enrolled and treated.

The active gel or placebo is applied twice a day to affected areas of the body for 12 weeks.

The capsules or tablets are orally administered to patients 1-4 times a day for 12 weeks.

The treatment results are evaluated at 2 week intervals until week 12 and then at 4 weeks after discontinuation of the study medication.

Criteria for Evaluation:

Safety:

Safety is evaluated by general history and physical signs, laboratory testing for hematology, serum chemistry, and urinalysis, and by evaluations of local application site tolerability parameters of erythema, scaling, dryness, stinging/burning utilizing a rating scale of “0” (None) to “3” (Severe).

Efficacy:

Efficacy is evaluated utilizing:

1. an overall assessment of disease severity at study entry and at 2 week intervals until week 12 and subsequently at 4 weeks after study medication discontinuation. The investigator global assessment, IGA, is based upon a rating scale of 0 to 4 with 0=none or clear, 1=almost clear, 2=mild disease involvement, 3=moderate disease involvement, and 4=severe disease involvement, and:

2. separate evaluation of a representative target psoriasis lesion for erythema, scaling, and thickness of each parameter rated on a 0-4 scale with 0=none or clear, 1=almost clear, 2=mild disease involvement, 3=moderate disease involvement, and 4=severe disease involvement.

Statistical analyses of each of the efficacy evaluations are performed for each of the 2 week study time points. Definitive evaluation of efficacy is based upon comparisons of active to vehicle groups at end of treatment at 12 weeks. The 4 week-post treatment evaluation is utilized to evaluate durability of treatment effect after medication discontinuation.

Example 20. Treatment of Acne (Prophetic Example)

Objectives:

To investigate the efficacy of the 3-(methylsulfonyl)acrylonitrile gel in patients having acne vulgaris.

Topical Formulation:

3-(methylsulfonyl)acrylonitrile is prepared as a gel formulation according to Example 3 or as a cream formulation according to Example 4. Active compounds in a gel or cream formulation are used in this experiment. Placebo contains the same gel or cream ingredients without the active compound.

Oral Formulation:

Capsules or tablets each containing 50-200 mg of the active compound (3-(methylsulfonyl)acrylonitrile are used in this example. Placebo capsules or tablets do not contain the active compound.

Methodology:

This is a randomized, double-blind, placebo controlled, parallel treatment clinical activity study.

Male and female patients with mild to severe acne vulgaris are enrolled. Patients discontinue all treatments for acne for a period of 4 weeks before initiation of the study. Patients are randomized in a 1:1 ratio (active gel, placebo). A total of 500 patients are enrolled and treated.

The active gel or placebo is applied twice a day to affected areas of the body for 12 weeks.

The capsules or tablets are orally administered to patients 1-4 times a day for 12 weeks. The treatment results are evaluated at 2 week intervals until week 12 and then at 4 weeks after discontinuation of the study medication.

Criteria for Evaluation:

Safety:

Safety is evaluated by general history and physical signs, laboratory testing for hematology, serum chemistry, and urinalysis, and by evaluations of local application site tolerability parameters of erythema, scaling, dryness, stinging/burning utilizing a rating scale of "0" (None) to "3" (Severe).

Efficacy:

Efficacy is evaluated utilizing:

1. an overall assessment of disease severity at study entry and at 2 week intervals until week 12 and subsequently at 4 weeks after discontinuation of the study medication. The investigator global assessment, IGA, is based upon a rating scale of 0 to 4 with 0=none or clear, 1=almost clear, 2=mild disease involvement, 3=moderate disease involvement, and 4=severe disease involvement, and:

2. separate counts of all types of acne lesions i.e. open and closed comedones, papules, pustules, nodules, and cysts.

Statistical analyses of each of the efficacy evaluations are performed for each of the 2 week study time points. Definitive evaluation of efficacy is based upon comparisons of active to vehicle groups at end of treatment at 12 weeks. The 4 week-post treatment evaluation is utilized to evaluate durability of treatment effect after medication discontinuation.

It is to be understood that the foregoing describes preferred embodiments of the present invention and that modifications may be made therein without departing from the scope of the present invention as set forth in the claims.

What is claimed is:

1. A method for treating pain, comprising:

administering to the subject suffering from pain an effective amount of morphine and an effective amount of 3-(methylsulfonyl)acrylonitrile.

2. The method according to claim 1, wherein said pain is nociceptive pain.

3. A method for potentiating the analgesic effects of morphine, comprising:

administering an effective amount of 3-(methylsulfonyl) acrylonitrile to a subject who is being treated with morphine and is suffering from pain.

4. The method according to claim 3, wherein said pain is nociceptive pain.

5. The method according to claim 3, wherein said administering is by oral administration.

* * * * *